(12) United States Patent
Bruder et al.

(10) Patent No.: US 7,286,629 B2
(45) Date of Patent: Oct. 23, 2007

(54) METHOD FOR TAKING TOMOGRAMS OF A BEATING HEART

(75) Inventors: Herbert Bruder, Hoechstadt (DE); Thomas Flohr, Uehlfeld (DE)

(73) Assignee: Siemens Aktiengesellschaft, Munich (DE)

( * ) Notice: Subject to any disclaimer, the term of this patent is extended or adjusted under 35 U.S.C. 154(b) by 167 days.

(21) Appl. No.: 11/119,750

(22) Filed: May 3, 2005

(65) Prior Publication Data
US 2005/0249328 A1    Nov. 10, 2005

(30) Foreign Application Priority Data
May 4, 2004   (DE)   ............. 10 2004 021 965

(51) Int. Cl.
*G21K 1/12* (2006.01)
(52) U.S. Cl. .............. 378/8; 378/4; 378/95; 378/901
(58) Field of Classification Search .......... 378/4–20, 378/95, 901
See application file for complete search history.

(56) References Cited

U.S. PATENT DOCUMENTS

| | | | | |
|---|---|---|---|---|
| 4,721,114 A * | 1/1988 | DuFault et al. | ............. | 600/509 |
| 6,243,437 B1 * | 6/2001 | Hu et al. | ............. | 378/8 |
| 6,327,326 B1 * | 12/2001 | Flohr et al. | ............. | 378/8 |
| 6,370,217 B1 * | 4/2002 | Hu et al. | ............. | 378/8 |
| 6,438,196 B1 * | 8/2002 | Cesmeli | ............. | 378/8 |
| 6,442,420 B1 * | 8/2002 | Julu et al. | ............. | 600/509 |
| 2003/0216641 A1 * | 11/2003 | Acharya et al. | ............. | 600/428 |
| 2004/0019275 A1 | 1/2004 | Iatrou et al. | ............. | 600/428 |
| 2004/0176697 A1 * | 9/2004 | Kappenberger et al. | ............. | 600/518 |
| 2004/0179644 A1 * | 9/2004 | Tsuyuki | ............. | 378/8 |

OTHER PUBLICATIONS

Stearns, S.D.: Digitale Verarbeitung analoger Signale, 3.Auflage, München (u.a.): Oldenbourg 1987, 297-301. ISBN: 3-486-203329-0.

* cited by examiner

*Primary Examiner*—Courtney Thomas
*Assistant Examiner*—Alexander Taningco
(74) *Attorney, Agent, or Firm*—Harness, Dickey & Pierce

(57) ABSTRACT

A method is for taking tomograms of a patient's beating heart with the aid of a computed tomography unit. ECG signals of the beating heart are recorded. In order to reconstruct the cardiac tomograms, use is made of detector data that originate from a selected cycle area of the cardiac cycle. The cycle area from which the data for the reconstruction originate is selected automatically and individually per cycle, for at least one cardiac cycle, by use of pattern recognition.

19 Claims, 3 Drawing Sheets

METHOD FOR TAKING TOMOGRAMS OF A BEATING HEART

The present application hereby claims priority under 35 U.S.C. §119 on German patent application number DE 10 2004 021 965.6 filed May 4, 2004, the entire contents of which is hereby incorporated herein by reference.

1. Field of the Invention

The invention generally relates to a method for taking tomograms of a patient's beating heart with the aid of a computed tomography unit. In one example embodiment, in order to scan the beating heart, at least one focus with an oppositely situated detector, preferably a multirow detector, is moved around the patient. Detector data output by the detector that represent the attenuation of the beams emanating from the at least one focus are then recorded together with indirect or direct spatial orientation data of the beams. ECG signals of the beating heart are recorded, these data and signals being stored in a temporally correlated fashion, if appropriate. Furthermore, in order to reconstruct the cardiac tomograms, use is made only of detector data that originate from a selected cycle area of the cardiac cycle.

2. Background of the Invention

Methods are generally known and are frequently applied in computed tomography. With these methods for ECG-gated CT pictures, there is basically, on the one hand, the possibility of using the heartbeat, in particular the ECG signal, for the purpose of carrying out the actual scan of the cardiac area only at time intervals at which there is as little movement as possible in the heart or cardiac area considered, and of using all data thus obtained to reconstruct CT tomograms. On the other hand, it is also proposed in part to scan the patient continuously. Once both the detector data and the ECG recorded simultaneously and in a correlated fashion have been collected, it is proposed to select from the existing data pool only the detector data that are provided with the datum of specific cycle phases, and to use them for later reconstruction of CT tomograms.

With both methods, the cycle phases considered are selected in the known systems by defining the start and end of a cardiac cycle by the characteristic R wave. Subsequently, the cycle area is set, considered relative to the R wave in an absolute time period in relation thereto, or in a percentage time period relative to the cycle duration.

Such a mode of procedure certainly fundamentally facilitates a substantial improvement of CT pictures of a beating heart by comparison with normal pictures which are not ECG-triggered. However, the problem of the known ECG triggering resides in the fact that instead of determining the actual beginning of movement of the heart region being examined and reliably gathering data from this cycle phase in order to produce images, the known recognition methods are oriented solely through the R waves of the ECG which do not, however, originally constitute the beginning of the cycle phase respectively considered. If, for example, the aim is to display the right-hand coronary vessel in a sharply defined fashion, it must be taken into account that the movement of the latter is sometimes influenced by the movement of the atria.

Again, it is known from U.S. patent application 2004/0019275 A1 to determine the most favorable phase area for data collection in an individual fashion per cardiac cycle. It is further proposed to supplement the R peak information and the heart rate of the patient with the use of additional statistical information relating to the shapes and intervals of the ECG contour. However, the method described there uses exclusively statistical data and, with the exception of the heart rate, does not take account of the individual properties owing to the respective particular patient.

SUMMARY OF THE INVENTION

It is an object of an embodiment of the invention to find a method for taking tomograms of a beating heart that provides a better definition of the heart phase respectively being considered.

In one embodiment, the inventors have realized that it is possible to improve ECG-triggered cardiac pictures if, instead of the rigid time-slot method used to date, which is oriented to the position of the R wave, or the use of other statistical evaluations over a multiplicity of patient data, a significant ECG signal profile of individual heart phases is automatically detected on the basis of a manually determined phase segment of the current ECG.

It has previously been assumed that the area of the cardiac cycle being looked for or considered is located in a time interval of the cardiac cycle that is defined in absolute or percentage terms relative the to R wave, in which case the influence of sex, age, medical circumstances or patient history have also been taken into account, if appropriate, by statistical surveys. No account has been taken of influences specific to individual patients, or influences stemming from particularities of the current measurement, for example, the positioning of the electrodes on the patient.

In one embodiment, an automatic, individual selection of the cycle area is now undertaken per cycle by manually marking a current P wave profile from the current ECG of the patient, and searching through each cardiac cycle with its ECG signal profile with reference to this manually selected ECG contour. Then, the most likely instant of the repeated occurrence of this contour is determined by the use of pattern recognition, in order to locate individually per cycle the desired cycle area in which the detector output data are used for reconstructing tomograms.

In one embodiment, with reference to the type of pattern recognition, the latter runs at least semiautomatically and in a computer-aided fashion such that there is no need for every individual heart cycle to be evaluated manually. For example, the typical signature of a P wave can be compared with the actual profile of the ECG signal, and the temporal position of the best correspondence can be determined. Once the latter has been determined, the beginning of the atrial excitation can be defined very precisely. Thus, it is possible to make use for the reconstruction only of detector data that precede this phase temporally in the cycle.

In order to support the manual selection, it is possible within the scope of the invention to make use of already known ECG analysis methods, such as are generally available for automatic evaluation of ECGs, in order to determine a cycle area to be used for the CT evaluation.

The inventors propose, in accordance with at least one embodiment, to make use of a computed tomography unit to improve a method known per se for taking tomograms of a patient's beating heart. To scan the beating heart, at least one focus with an oppositely situated detector, preferably a multirow detector, is moved around the patient; detector data output by the detector that represent the attenuation of the beams emanating from the at least one focus are recorded together with indirect or direct spatial orientation data of the beams; and ECG signals of the beating heart are recorded. These data and signals are stored in a temporally correlated fashion, if appropriate. Furthermore, in order to reconstruct the cardiac tomograms, use is made only of detector data that originate from a selected cycle area of the cardiac cycle, the cycle area from which the data for the reconstruction originate being selected automatically and individually per cycle for at least one cardiac cycle by pattern recognition.

An inventive improvement, in at least one embodiment, resides in the fact that the cycle area from which the data for the reconstruction originate may be selected automatically and individually per cycle by pattern recognition for at least one cardiac cycle. In this case, before the automatic selection of the cycle area from which detector data are used for the reconstruction is carried out, a typical signal profile of the current ECG in this area or an adjacent one may be determined manually. This typical profile may be subsequently automatically detected again in at least one cardiac cycle to which the determination of the desired area is oriented for the reconstruction.

Such an individual consideration of each separate cardiac cycle, and the substantially more precise determination, resulting therefrom, of the useful cycle area for reconstructing computed tomography pictures advantageously leads to the CT pictures obtained in such an at least one embodiment, having fewer artifacts and blurs than typically occurs in the known systems.

The manual selection of the cycle area to be considered in a reference cycle can be performed by visual recognition of the corresponding cycle area on a display screen or some other suitable display unit. In this case, the selection of this typical signal profile should be undertaken from the same ECG and the same measurement on a patient in which the automatic determination of the area subsequently takes place in further cycles, since it is possible thereby to avoid any changes that may occur from different positioning of electrodes or other metrological differences.

It is particularly favorable in the case of the method according to at least one embodiment of the invention, to make use of the profile of a P wave as typical signal profile. This is because the beginning of the P wave constitutes the beginning of the excitation of the atria, which means that the beginning of a detected typical area can simultaneously be defined as temporal end of a temporal scanning area in a cycle.

For example, the method according to an embodiment of the invention can be carried out in the following steps:

a time sector is marked manually in a cycle in a visualized ECG, and the profile, located in said sector, of the ECG is adopted as typical signal profile $S_p$ of a P wave (=template);

subsequently, the typical signal profile $S_p$ is automatically compared with the actual signal profile $E_p$ of further cycles of the ECG by means of successively temporally offset convolution, for example by calculating $$P_1(t) = S_p \otimes E_p(t) = \frac{1}{N} \cdot \int_{-(tt_s+tt_e)/2}^{(tt_s+tt_e)/2} d\tau \cdot h_c \cdot S_p(\tau) \cdot E_p(t-\tau) t \in p_1$$

with the normalization factor N, for which it holds that:

$$N = \int_{-(tt_s+tt_e)/2}^{(tt_s+tt_e)/2} d\tau \cdot S_p(\tau)^2,$$

with the variables for the start $tt_S$ and the end $tt_e$ of the cycle interval in which the pattern to be determined is presumed, the integration variables $\tau$ in the time interval considered, the time t and the cycle $p_I$ considered;

a greatest maximum is determined per cycle in the temporal profile of the convolution function $P_I(t)$, preferably the normalized convolution function, the actual position of the P wave per cycle, and thus the temporal end of the rest phase of the atrium of the heart per cycle, being determined therefrom, in which case only data of a cycle before the end thus determined of the rest phase is used to reconstruct CT image data.

It may be pointed out that it is fundamentally advantageous in the abovenamed example for the convolution function $P_I(t)$ to be normalized, although this is not mandatory for the purpose of an embodiment of the invention. If such a normalization is carried out, it is possible to specify in a particularly simple way a minimum of the convolution function that must be reached in order to have actually found reliably a signal profile in the cardiac cycle considered that is identical to the typical signal profile. It is therefore possible to specify or define a threshold value that, should it not be reached upon comparison of the typical signal profile and the current signal profile of the ECG, leads on to another recognition method or, if appropriate, reserves this cycle in the event of sufficient redundancy for the reconstruction.

With reference to pattern recognition methods that can be used for the method according to an embodiment of the invention, reference may be made, by way of example, to the principle of wavelet transformation as it is known in essence for ECG analysis algorithms. However, it is also possible to find the prescribed contour again by applying a neural network in the respective cardiac cycle.

Of course, embodiments of the invention extend not only to the method according to an embodiment of the invention, but also to the use of the method in a tomograph. It is also possible to implement the method according to an embodiment of the invention by way of appropriate programs or program modules.

BRIEF DESCRIPTION OF THE DRAWINGS

Embodiments of the invention are explained in more detail below with the aid of the figures, the following abbreviations being used in the figures: 1: computed tomography unit; 2: X-ray tube; 3: detector; 4: system or z-axis; 5: housing; 6: patient couch; 7: patient; 8: measuring lead; 9: computer; 9.1: display screen; 9.2: input unit; 10: data and control line; 11: P waves; 12: Q wave; 13: R wave; 14: S wave; 15: QRS complex; 16: T wave; 17: U wave; 18: PQ time; 19: ST segment; 20: QT duration; 21: distance; 22: ECG signal profile; 23: area of the actual signal profile; 24: area of typical signal profile; 25: graph; 26: maximum; $P_1$-$P_n$, programs; $T_{RR}$: heart rate; $\tau$: time in time intervals; $\tau_{max}$: instant of maximum coverage.

In detail.

DETAILED DESCRIPTION OF THE EXAMPLE EMBODIMENTS

Figure 1:
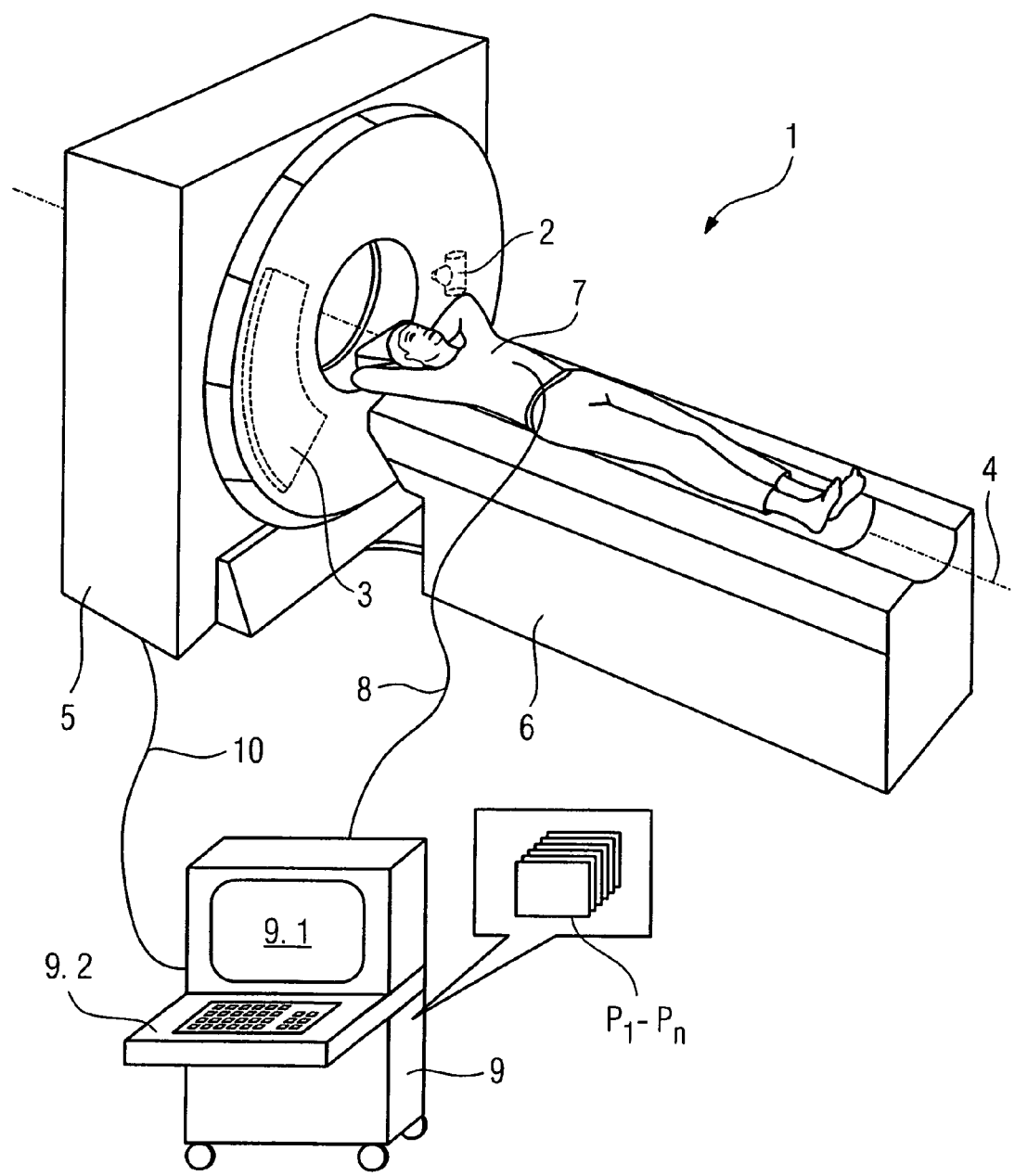
FIG. 1 shows an illustration of a tomograph for carrying out the method according to an embodiment of the invention.

FIG. 1 shows a 3-D illustration of one embodiment including a computed tomography unit 1 having an X-ray tube 2 and a detector 3 situated opposite the latter, which are fastened on a rotary frame (not visible) and are designed such that they can rotate about a system axis or z-axis 4. The patient 7 may be located on a patient couch or table 6, for example, that can be displaced along the z-axis 4. While the X-ray tube 2 and the detector 3 are rotating about the system axis 4, is the patient may be pushed along this system axis 4 through an opening in the housing 5 of the computed tomography unit 1 (or vice versa), such that the X-ray tube 2 and the detector 3 move relative to the patient on a spiral track around the patient, thus effecting scanning.

It is to be noted in principle that other variants of the scanning are also possible. Thus, for example, scanning may be done sequentially by moving the X-ray tube 2 and the detector 3 in a circle around the patient 7 and performing a discrete advance of the patient along the system axis 4 after a complete circular scan. Thereafter, a circular scan is again carried out until the patient or at least the examination area considered, is completely scanned.

If a detector with a large number of detector rows, that is to say with a large extent in the direction of the z-axis, is used, it is therefore possible, if appropriate, also to scan at least the heart area under particular consideration here with the aid of a single rotation of the detector. All described variants for the spiral or sequential circular scanning and detectors ranging from a single row to a multiplicity of rows can be used in conjunction with the method according to embodiments of the invention.

In addition to scanning the patient with X-rays, the patient's cardiac activity may be recorded by use of electrodes (not illustrated individually) and a measuring lead 8 in an ECG. This ECG is located in the present example in a computer 9 and simultaneously also controls the tomograph or computed tomography unit 1. In addition to controlling the tomograph and the taking of an ECG, the computer 9 also serves for evaluating and, if appropriate, storing the detector output data, which is performed via a data and control line 10.

The computer 9 can be used, furthermore, to carry out the reconstruction of the tomograms. The schematically illustrated programs $P_1$ to $P_n$ serve this purpose, it being possible to illustrate the results on the display screen 9.1 integrated in the computer 9. The input unit 9.2, for example in the form of a keyboard and/or a mouse (not illustrated explicitly here), can serve for inputting data in order to operate the tomograph.

Figure 2:
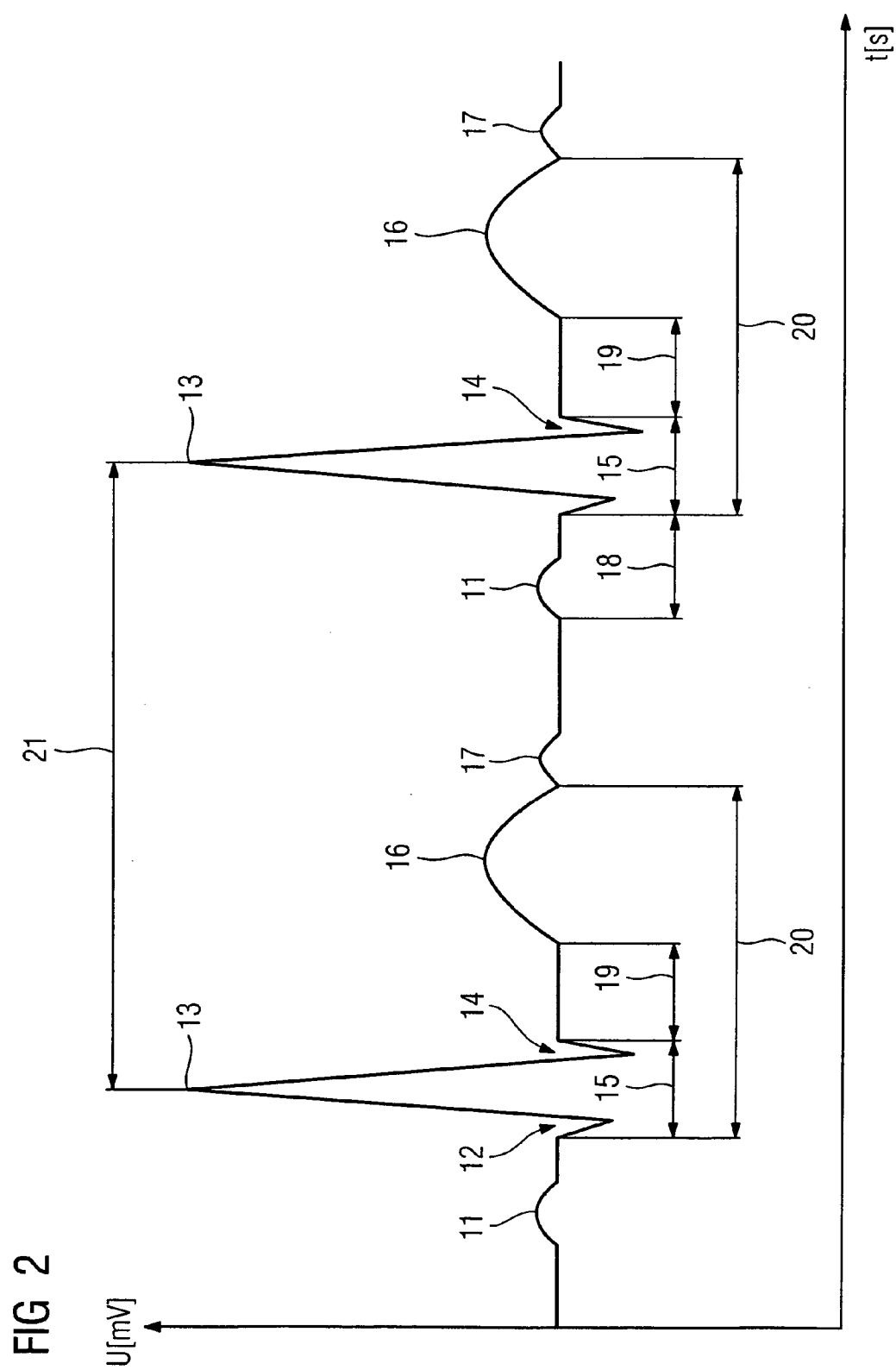
FIG. 2 shows an idealized signal profile of a typical ECG.

A typical and idealized ECG is illustrated in FIG. 2 for the purpose of understanding the embodiments of the invention better. Here, the time t in seconds is plotted on the abscissa and the detected potential in mV is plotted on the ordinate. A typical ECG is distinguished by a characteristic signal profile of the voltage peaks and troughs over time, and provides information on the situation regarding the transmission of impulses, regarding excitation and regarding movement of the heart. The typical signal contours are described below with the aid of the reference symbols.

Numeral 11 denotes the P wave. The P wave is characteristically the first small, positive, semicircular wave after the zero line. It represents the excitation of the atria.

Numeral 12 denotes the Q wave. The Q wave is generally small, that is to say neither broad nor deep, and represents the first negative wave after the P wave and the end of the PQ time. The Q wave denotes the beginning of the ventricular excitation.

Numeral 13 denotes the R wave. The R wave is always narrow and high. It is the first positive wave after the Q wave, or the first positive wave after the P wave should the Q wave be missing. The R wave is an expression of the ventricular excitation.

Numeral 14 denotes the S wave. The S wave is usually small, like the Q wave. It is the first negative wave after the R wave and likewise belongs to the ventricular excitation.

Numeral 15 denotes the QRS complex. The QRS complex denotes the ventricular excitation, that is to say depolarization, of the ventricles. Beginning in parallel with the depolarization of the ventricles is the repolarization of the atria, but this voltage pulse vanishes in the QRS complex.

Numeral 16 denotes the T wave. The T wave is relatively wide, large and semicircular, and represents the first positive swing after the QRS complex. It corresponds to the excitation recovery, that is to say repolarization, of the ventricles. After the end of the T wave an electrical heartbeat ends. The next cycle then arises after a specific pause. The higher the heart rate, the shorter this distance.

Numeral 17 denotes the U wave. The U wave is a very small, positive, semicircular wave just after the T wave, and is not always visible. It corresponds to subsequent fluctuations in the ventricular excitation recovery. In addition to the individual waves in the ECG, the times between the waves are also important for an interpretation.

Numeral 18 denotes the PQ time. The PQ time (segment) stretches from the beginning of the P wave up to the beginning of the Q or R wave (in the event of lack of the R wave). It represents the atrioventricular conduction time, that is to say the excitation conduction time from the atria to the ventricles.

Numeral 19 denotes the ST time. The ST time (segment) stretches from the end of the S or R wave (in the event of lack of the S wave) up to the beginning of the T wave. It indicates the beginning of the excitation recovery of the ventricles.

Numeral 20 denotes the QT duration. The QT time (segment) comprises the QRS complex, the ST segment and the T wave. The time from the beginning of the ventricular excitation up to the end of the excitation recovery of the ventricles corresponds to the electrical ventricular systole.

The heart rate $T_{RR}$ is determined by the distance 21 between two R waves 13 in the ECG.

The temporal position of all the individual segments of the ECG that are illustrated can be determined by a comparison of a typical voltage profile above the time axis, that is to say a typical contour, with the actual ECG profile. However, it is to be noted that in the event of pathological changes, changes that have to be taken into account correspondingly also occur in the contour of the ECG signal. It is advantageous here, in particular, not to make use of a general standard as signal profile for the cycle phase being considered, but to make use of the most typical example possible from the ECG signal of the patient being examined, as far as possible from the same ECG, since thereby not only is account taken of differences with reference to the particular situation concerning the transmission of impulses of the heart being considered, but also possible differences in the attachment of the electrodes to the patient come into play.

Figure 3:
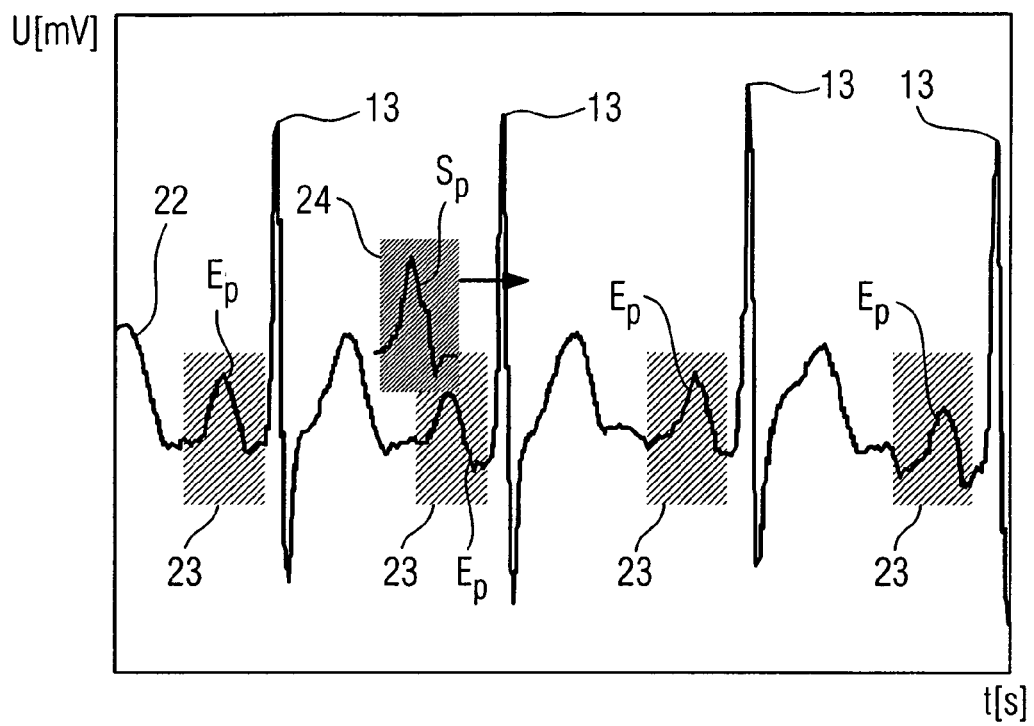
FIG. 3 shows a schematic of an automated pattern recognition of a P wave in an ECG.

By contrast with the signal profile of FIG. 2, which illustrates an idealized situation of an ECG, FIG. 3 illustrates an example of an actual ECG signal profile 22 of a patient such as is used for triggering a cardio CT. The signal profile exhibits four R waves and, correspondingly, three complete periods or cardiac cycles of the heart being examined. Each of the four R waves 13 is given a hatched background area 23 in which it can be assumed that a P wave is located there solely on the basis of temporal consideration of the ECG signal, and of the distance from the R wave following thereupon or preceding it.

Illustrated in the area 24 is a typical P wave of the corresponding patient, which originates from a cycle before that and has been selected by the operator as a typical P wave and is now being used for accurate determination of the position of the P wave in the respective current cardiac cycle. For this purpose, the typical signal profile 24 is temporally shifted over the area 23, and the individual signal values of the actual signal profile and of the typical signal profile are multiplied by one another, the sum of the multiplication values of the two signals being calculated at each instant τ of the shifting of the typical signal profile with respect to the current signal profile.

Figure 4:
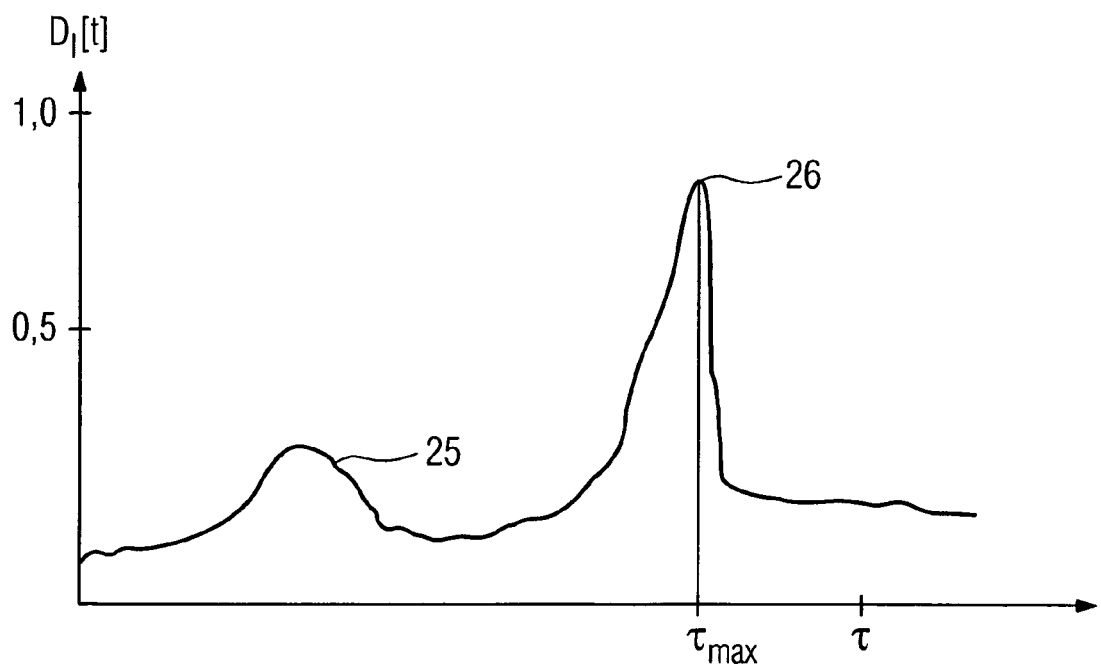
FIG. 4 shows the temporal profile of a convolution function in the case of a pattern comparison.

FIG. 4 shows the profile of such a convolution function $P_f(t)$ plotted against the respective temporal shift τ between the typical signal profile and the current signal. It is to be seen from the graph 25, which illustrates the value of this convolution function $P_f(t)$ as a function of τ, that the function reaches a maximum as soon as the typical signal profile 24 is largely congruent with the actual signal profile 23 of the P wave. Since the convolution function $P_f(t)$ is normalized, it reaches the value 1 when complete congruence of the two signal profiles is achieved.

The maximum 26 shown reproduces the instant $\tau_{max}$ at which there is an optimum coverage of the two signal profiles. It thereby determines the actual position of the typical signal profile being sought, here that of a P wave, in a cardiac cycle being considered. This instant $\tau_{max}$ can now be used to specify the exact position of the P wave or some other typical signature in the cardiac cycle, and so it is possible thereafter to determine, in a very differentiated way, at which instant, or in which cycle area, the CT data obtained can be used for the reconstruction.

It is self-evident that the above-named features of embodiments of the invention can be used not only in the combination respectively specified, but also in other combinations or on their own, without departing from the scope of the invention.

Thus, overall, at least one embodiment of the invention describes a method for taking tomograms of a patient's beating heart with the aid of a computed tomography unit, in the case of which ECG signals of the beating heart are recorded. Further, in order to reconstruct the cardiac tomograms, use is made only of detector data that originate from a selected cycle area of the cardiac cycle, the cycle area from which the data for the reconstruction originate being selected automatically and individually per cycle for at least one cardiac cycle by pattern recognition. Thus, by comparing a typical ECG pattern of a cardiac phase with the current ECG of a patient during the CT scan, at least one embodiment of the invention supplies the temporal determination of a prescribed cardiac phase in an essentially improved fashion by comparison with the known systems, and thereby also supplies an improvement in the ECG-triggered reconstruction of CT pictures.

Any of the aforementioned methods may be embodied in the form of a system or device, including, but not limited to, any of the structure for performing the methodology illustrated in the drawings.

Further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable non-volatile memory, such as memory cards; and media with a built-in ROM, such as ROM cassettes.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for taking tomograms of a patient's beating heart with the aid of a computed tomography unit, the method comprising:

moving at least one focus, with an oppositely situated detector, around the patient to scan the beating heart;

recording detector data, output by the detector and representing an attenuation of the beams emanating from the at least one focus, together with indirect or direct spatial orientation data of the beams;

recording ECG signals of the beating heart, the detector data and ECG signals being stored in a temporally correlated fashion; and using, to reconstruct the tomograms, detector data that originates from a selected cycle area of a cardiac cycle of the heart, the cycle area being selected automatically and individually per cycle for at least one cardiac cycle by pattern recognition, wherein the using includes before the automatic selection of the cycle area is carried out, a typical signal profile of the current ECG in at least one of the area and an adjacent one is determined manually, and the typical profile is subsequently automatically detected again in at least one cardiac cycle to which the determination of the desired area is oriented for the reconstruction.

2. The method as claimed in claim 1, wherein the profile of a P wave is used as typical signal profile.

3. The method as claimed in claim 2, further comprising:

manually marking a time sector in a cycle in a visualized ECG, the profile, located in the sector, of the EGG being adopted as typical signal profile of a P wave (template $S_p$);

subsequently automatically comparing the typical signal profile $S_p$ with the signal profile $E_p$ of further cycles of the EGG via a convolution function $P_f(t)$ that corresponds to a successively temporally offset convolution;

determining a greatest maximum per cycle in the temporal profile of the convolution function $P_f(t)$, the actual position of the P wave per cycle, and thus the temporal end of the rest phase of the atrium of the heart per cycle, being determined therefrom.

4. The method as claimed in claim 2, wherein the cycle area whose data are used for the reconstruction precedes the detected area of the P wave.

5. The method as claimed in claim 2, wherein a neural network is used to compare the contour of the profile of the EGG signal with a prescribed contour.

6. The method as claimed in claim 2, wherein, for a cycle in which no P wave position is to be determined, the cycle area considered is determined by at least one known method.

7. The method as claimed in claim 3, wherein the successively temporally offset convolution is performed by calculating $$P_1(t) = S_p \otimes E_p(t) = \frac{1}{N} \cdot \int_{-(tt_s+tt_e)/2}^{(tt_s+tt_e)/2} d\tau \cdot h_c \cdot S_p(\tau) \cdot E_p(t-\tau) t \in p_1$$

where:

$$N = \int_{-(tt_s+tt_e)/2}^{(tt_s+tt_e)/2} d\tau \cdot S_p(\tau)^2$$

and $tt_S$ is the start and $tt_e$ is the end of a cycle interval in which the pattern to be determined is presumed, $\tau$ is the integration variable in the time interval considered, t is the time, and $p_l$ is the cycle considered.

8. The method as claimed in claim 7, wherein the convolution function $P_l(t)$ is normalized.

9. The method as claimed in claim 8, wherein the cycle area whose data are used for the reconstruction precedes the detected area of the P wave.

10. The method as claimed in claim 7, wherein the cycle area whose data are used for the reconstruction precedes the detected area of the P wave.

11. The method as claimed in claim 3, wherein the convolution function $P_l(t)$ is normalized.

12. The method as claimed in claim 11, wherein the cycle area whose data are used for the reconstruction precedes the detected area of the P wave.

13. The method as claimed in claim 3, wherein the cycle area whose data are used for the reconstruction precedes the detected area of the P wave.

14. The method as claimed in claim 3, wherein a neural network is used to compare the contour of the profile of the EGG signal with a prescribed contour.

15. The method as claimed in claim 3, wherein, for a cycle in which no P wave position is to be determined, the cycle area considered is determined by at least one known method.

16. The method as claimed in claim 1, wherein a neural network is used to compare the contour of the profile of the ECG signal with a prescribed contour.

17. The method as claimed in claim 1, wherein, for a cycle in which no P wave position is to be determined, the cycle area considered is determined by at least one known method.

18. The method as claimed in claim 1, wherein the detector is a multirow detector.

19. A computer readable medium, including executable instructions, which when executed by a computer, cause the computer to perform the method of claim 1.

* * * * *